(12) United States Patent
Horan et al.

(10) Patent No.: US 12,402,923 B2
(45) Date of Patent: Sep. 2, 2025

(54) OFFSET HOLE FOR TPLO COMPRESSION

(71) Applicant: DEPUY SYNTHES PRODUCTS, INC., Raynham, MA (US)

(72) Inventors: Timothy J. Horan, Royersford, PA (US); Michael Kowaleski, Harwich, MA (US); Jaime Mazurek, West Chester, PA (US); James Guthlein, Malvern, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 520 days.

(21) Appl. No.: 17/937,954

(22) Filed: Oct. 4, 2022

(65) Prior Publication Data
US 2024/0108385 A1    Apr. 4, 2024

(51) Int. Cl.
*A61B 17/80* (2006.01)

(52) U.S. Cl.
CPC ...... *A61B 17/8014* (2013.01); *A61B 17/8061* (2013.01)

(58) Field of Classification Search
CPC .............. A61B 2017/681; A61B 17/80; A61B 17/8004; A61B 17/8014; A61B 17/8061
See application file for complete search history.

(56) References Cited

U.S. PATENT DOCUMENTS

| | | |
|---|---|---|
| RE31,628 E | 7/1984 | Allgower et al. |
| 4,565,191 A | 1/1986 | Slocum |
| 4,677,973 A | 7/1987 | Slocum |
| 4,762,122 A | 8/1988 | Slocum |

(Continued)

FOREIGN PATENT DOCUMENTS

| | | |
|---|---|---|
| DE | 10015734 A1 | 9/2001 |
| EP | 1 986 557 | 7/2010 |

(Continued)

OTHER PUBLICATIONS

Synthes, "Mini Tibial Plateau Leveling Osteotomy (TPLO) Plate System. For stabilizing osteotomies of the canine and feline proximal tibia. Technical Guide", Synthes, Inc., 2012, 29 sheets.
DePuy Syntes Vet, "Mini Tibial Plateau Leveling Osteotomy (TPLO) System. Surgical Technique", 2013, 32 sheets.
DePuy Syntes, "Variable Angle Locking Hand System. Surgical Technique", 2021, 89 sheets.

(Continued)

*Primary Examiner* — Larry E Waggle, Jr.
(74) *Attorney, Agent, or Firm* — Fay Kaplun & Marcin, LLP

(57) ABSTRACT

TPLO plate includes first and second distal holes and a body with a proximal portion positioned over a proximal tibia segment and a distal portion extending along a longitudinal axis and positioned over a distal tibia segment. The first hole includes an elongated portion extending along the longitudinal axis and an offset portion extending distally from the elongated portion along an offset axis at an angle relative to the longitudinal axis. The second hole extends through the distal portion along the longitudinal axis in alignment with the elongated portion and includes a sloped compression surface along a distal portion. The first hole is such that, when a distal compression to osteotomy cut is applied via insertion of a bone fixation element into the distal portion, the element translates along the offset axis from a central axis to an intersection point to provide a cranial compression to the cut.

19 Claims, 3 Drawing Sheets

(56) References Cited

U.S. PATENT DOCUMENTS

| | | |
|---|---|---|
| 4,800,874 A | 1/1989 | David et al. |
| 4,867,144 A | 9/1989 | Karas et al. |
| 4,955,888 A | 9/1990 | Slocum |
| 4,988,350 A | 1/1991 | Herzberg |
| 5,002,544 A | 3/1991 | Klaue et al. |
| 5,190,544 A | 3/1993 | Chapman et al. |
| 5,304,180 A | 4/1994 | Slocum |
| 5,364,398 A | 11/1994 | Chapman et al. |
| 5,578,038 A | 11/1996 | Slocum |
| 5,601,553 A | 2/1997 | Trebing et al. |
| 5,709,686 A | 1/1998 | Talos et al. |
| 5,733,287 A | 3/1998 | Tepic et al. |
| 5,749,872 A | 5/1998 | Kyle et al. |
| 5,752,953 A | 5/1998 | Slocum |
| 5,827,286 A | 10/1998 | Incavo et al. |
| 5,868,749 A | 2/1999 | Reed |
| 5,904,684 A | 5/1999 | Rooks |
| 5,938,664 A | 8/1999 | Winquist et al. |
| 5,951,557 A | 9/1999 | Luter |
| 5,968,047 A | 10/1999 | Reed |
| 6,001,099 A | 12/1999 | Huebner |
| 6,077,266 A | 6/2000 | Medoff |
| 6,093,201 A | 7/2000 | Cooper et al. |
| 6,096,040 A | 8/2000 | Esser |
| 6,183,475 B1 | 2/2001 | Lester et al. |
| 6,221,073 B1 | 4/2001 | Weiss et al. |
| 6,283,969 B1 | 9/2001 | Grusin et al. |
| 6,623,486 B1 | 9/2003 | Weaver et al. |
| 6,669,701 B2 | 12/2003 | Steiner et al. |
| 6,719,759 B2 | 4/2004 | Wagner et al. |
| 6,974,461 B1 | 12/2005 | Wolter |
| 7,090,676 B2 | 8/2006 | Huebner et al. |
| 7,108,697 B2 | 9/2006 | Mingozzi et al. |
| 7,128,744 B2 | 10/2006 | Weaver et al. |
| D536,453 S | 2/2007 | Young et al. |
| 7,189,237 B2 | 3/2007 | Huebner |
| 7,195,633 B2 | 3/2007 | Medoff et al. |
| 7,267,678 B2 | 9/2007 | Medoff |
| 7,335,204 B2 | 2/2008 | Tornier |
| 7,341,589 B2 | 3/2008 | Weaver et al. |
| 7,537,596 B2 | 5/2009 | Jensen |
| 7,655,029 B2 | 2/2010 | Niederberger et al. |
| 7,695,502 B2 | 4/2010 | Orbay et al. |
| 7,722,653 B2 * | 5/2010 | Young .............. A61B 17/8014 |
| | | 606/291 |
| 7,740,648 B2 | 6/2010 | Young et al. |
| 7,951,179 B2 | 5/2011 | Matityahu |
| 8,177,818 B2 | 5/2012 | Wotton, III |
| 8,523,921 B2 | 9/2013 | Horan et al. |
| 10,226,288 B2 | 3/2019 | Sidebotham et al. |
| 10,258,396 B2 | 4/2019 | Kazanovicz et al. |
| 10,299,841 B2 | 5/2019 | Dunlop et al. |
| 10,582,958 B2 * | 3/2020 | Wotton ............. A61B 17/8052 |
| 11,096,729 B2 | 8/2021 | Dunlop et al. |
| D945,623 S | 3/2022 | Daye |
| 11,298,167 B2 | 4/2022 | Dunlop et al. |
| 11,357,553 B2 * | 6/2022 | Paton ............... A61B 17/8061 |
| 2002/0013587 A1 | 1/2002 | Winquist et al. |
| 2002/0045901 A1 | 4/2002 | Wagner et al. |
| 2002/0156474 A1 | 10/2002 | Wack et al. |
| 2004/0059335 A1 | 3/2004 | Weaver et al. |
| 2004/0116930 A1 | 6/2004 | O'Driscoll et al. |
| 2004/0167522 A1 | 8/2004 | Niederberger et al. |
| 2004/0193165 A1 | 9/2004 | Orbay |
| 2004/0225291 A1 | 11/2004 | Schwammberger et al. |
| 2004/0260291 A1 | 12/2004 | Jensen |
| 2005/0010226 A1 | 1/2005 | Grady, Jr. et al. |
| 2005/0015089 A1 | 1/2005 | Young et al. |
| 2005/0107796 A1 | 5/2005 | Gerlach et al. |
| 2005/0234458 A1 | 10/2005 | Huebner |
| 2005/0240187 A1 | 10/2005 | Huebner et al. |
| 2006/0009771 A1 | 1/2006 | Orbay et al. |
| 2006/0129151 A1 | 6/2006 | Allen et al. |
| 2006/0149275 A1 | 7/2006 | Cadmus |
| 2006/0173458 A1 | 8/2006 | Forstein et al. |
| 2006/0241608 A1 | 10/2006 | Myerson et al. |
| 2006/0264949 A1 | 11/2006 | Kohut et al. |
| 2007/0083204 A1 | 4/2007 | Sidebotham |
| 2007/0123886 A1 | 5/2007 | Meyer et al. |
| 2007/0162016 A1 | 7/2007 | Matityahu |
| 2007/0233106 A1 | 10/2007 | Horan et al. |
| 2008/0249573 A1 | 10/2008 | Buhren et al. |
| 2008/0300637 A1 | 12/2008 | Austin et al. |
| 2013/0204307 A1 | 8/2013 | Castaneda et al. |
| 2016/0128745 A1 | 5/2016 | Sidebotham et al. |
| 2019/0374266 A1 | 12/2019 | Paton |
| 2021/0085380 A1 | 3/2021 | Daye |
| 2021/0212738 A1 | 7/2021 | Daye |
| 2021/0298806 A2 | 9/2021 | Daye |
| 2021/0361331 A1 | 11/2021 | Daye |
| 2023/0140439 A1 | 5/2023 | Horan |
| 2023/0142959 A1 * | 5/2023 | Zysk .................. A61B 17/8057 |
| | | 606/282 |

FOREIGN PATENT DOCUMENTS

| | | |
|---|---|---|
| FR | 2405062 | 5/1979 |
| FR | 2405705 | 5/1979 |
| FR | 2406429 | 5/1979 |
| FR | 2758712 | 7/1998 |
| WO | 96/24295 | 8/1996 |
| WO | 01/19267 | 3/2001 |
| WO | 03/013623 | 2/2003 |
| WO | 2004/024009 | 3/2004 |
| WO | 2005/048888 | 6/2005 |
| WO | 2007/137437 | 12/2007 |
| WO | 2015/069728 | 5/2015 |
| WO | 2021/221920 | 11/2021 |

OTHER PUBLICATIONS

Looi et al., "Effects of Angled Dynamic Compression Holes in a Tibial Plateau Levelling Osteotomy Plate on Cranially Directed Fragment Displacement", Feb. 16, 2023, 6 sheets.

AO Development. "New Products from AO Development". News—No. 1, AO Publishing, Jun. 2004, 28 sheets.

Auer et al., "History of AOVET: The First 40 Years", AO Foundation, 2013, 96 sheets.

Ballagas et al., "Pre- and Postoperative Force Plate Analysis of Dogs with Experimentally Transected Cranial Cruciate Ligaments Treated Using Tibial Plateau Leveling Osteotomy", Veterinary Surgery, vol. 33, 2004, pp. 187-190.

Declaration of Troy D. Drewry regarding Claims 1-11, 19, 20 of U.S. Pat. No. 8,523,921, Jul. 12, 2019, 132 sheets.

Declaration of Jeffrey N. Peck, DVM, DACVS regarding Claims 1-11, 19, 20 of U.S. Pat. No. 8,523,921, Jul. 11, 2019, 123 sheets.

*DePuy Synthes Products, Inc. v. Veterinary Orthopedic Implants, Inc.*, No. 3-18-cv-01342-HES-PDB (M.D. Fla.), Redacted Excerpts from Plaintiff's Infringement Contentions, Dec. 14, 2022, 5 sheets.

Ganesh et al., "Biomechanics of bone-fracture fixation by stiffness-graded plates in comparison with stainless-steel plates", BioMedical Engineering OnLine, Jul. 2005, 4:46, 15 sheets.

Harasen, "Tibial Plateau Leveling Osteotomy—Part 1", Canadian Veterinary Journal, vol. 45, Jun. 2004, 2 sheets.

Harasen, "Tibial Plateau Leveling Osteotomy—Part 2", Canadian Veterinary Journal, vol. 45, Aug. 2004, 2 sheets.

Image Processing of Canine Tibia Medial Radius, Jun. 28, 2019, 21 sheets.

Ismail et al., "Outcome of Cloverleaf Locking Plate Fixation for Femoral Neck Fractures in Young Adults", Malaysian Orthopaedic Journal 2012, vol. 6, No. 1, pp. 30-34.

Jorgensen Laboratories Inc., "JorVet TPLO plate advertisement", ACVS Veterinary Surgery Medical Journal, vol. 34, No. 5, Sep.-Oct. 2005, 2 sheets.

Kergosien et al., "Radiographic and Clinical Changes of the Tibial Tuberosity after Tibial Plateau Leveling Osteotomy", Veterinary Surgery, vol. 33, 2004, pp. 468-474.

Krishnakanth, "Mechanical Considerations in Fracture Fixation", Queensland University of Technology, Brisbane, Australia, 2012, 192 sheets.

(56) References Cited

OTHER PUBLICATIONS

Le, "Biomechanics of Fractures and Fixation", Orthopaedic Trauma Association, 2004, 72 sheets.
New Generation Devices, "UCP-Unity Cruciate Plate", New Generation Devices, 2004, 2 sheets.
Newton et al., "Textbook of Small Animal Orthopaedics", J. B. Lippincott Company, 1985, 46 sheets.
Pacchiana et al., "Surgical and postoperative complications associated with tibial plateau leveling osteotomy in dogs with cranial cruciate ligament rupture: 397 cases (1998-2001)", JAVMA, vol. 222, No. 2, Jan. 15, 2003, pp. 184-193.
Palmer, "Understanding tibial plateau leveling osteotomies in dogs", Veterinary Medicine, Jun. 2005, vol. 100, No. 6, pp. 426-453.
Priddy et al., "Complications with and owner assessment of the outcome of tibial plateau leveling osteotomy for treatment of cranial cruciate ligament rupture in dogs: 193 cases (1997-2001)", JAVMA, vol. 222, No. 12, Jun. 15, 2003, pp. 1726-1732.
Petition for Inter Partes Review of Claims 1-11 of U.S. Pat. No. 8,523,921, Veterinary Orthopedic Implants, Inc., Jul. 12, 2019, 78 sheets.
Petition for Inter Partes Review of Claims 12-18 of U.S. Pat. No. 8,523,921, Veterinary Orthopedic Implants, Inc., Jul. 12, 2019, 72 sheets.
Petition for Inter Partes Review of Claims 19 and 20 of U.S. Pat. No. 8,523,921, Veterinary Orthopedic Implants, Inc., Jul. 12, 2019, 75 sheets.
Decision denying VOI's Petition for Inter Partes Review of claims 1-11 of U.S. Pat. No. 8,523,921, USPTO, PTAB, Jan. 21, 2020, 35 sheets.
Decision denying VOI's Petition for Inter Partes Review of claims 12-18 of U.S. Pat. No. 8,523,921, USPTO, PTAB, Jan. 22, 2020, 52 sheets.
Decision denying VOI's Petition for Inter Partes Review of claims 19-20 of U.S. Pat. No. 8,523,921, USPTO, PTAB, Jan. 22, 2020, 36 sheets.
VOI's Supplemental Invalidity Contentions re U.S. Pat. No. 8,523,921, USDC for the Middle District of Florida, Case No. 3:18-CV-01342, Sep. 18, 2019, 54 sheets.
Reif et al., "Comparison of Tibial Plateau Angles in Normal and Cranial Cruciate Deficient Stifles of Labrador Retrievers", Veterinary Surgery, vol. 32, 2003, pp. 385-389.
Reif et al., "Influence of Limb Positioning and Measurement Method on the Magnitude of the Tibial Plateau Angle", Veterinary Surgery, vol. 33, 2004, pp. 368-375.
Slatter, "Textbook of Small Animal Surgery"—3rd ed., Elsevier Science, 2003, 13 sheets.
Smith & Nephew, Inc., "TC-100 Screw & Plating System Catalog", USA, May 1999, 86 sheets.
Staubli et al., "TomoFix: a New LCP-Concept for Open Wedge Osteotomy of the Medial Proximal Tibia—Early Results in 92 Cases", Injury, International Journal of the Care of the Injured 34, 2003, 8 sheets.
Securos, Securos Orthopedic Implant Advertisements, ACVS Veterinary Surgery Medical Journal, 2003, 9 sheets.
Stoffel et al., "Open Wedge High Tibial Osteotomy: Biomechanical Investigation of the Modified Arthrex Osteotomy Plate (Puddu Plate) and the TomoFix Plate", Clinical Biomechanics 19, 2004, pp. 944-950.
Synthes, "Philos + Philos Long. The Anatomic fixation system for the proximal humerus with angular stability. Surgical Technique", Stratec Medical, 2005, 18 sheets.
Synthes Catalog—Part 1, 2002, pp. 1-300.
Synthes Catalog—Part 2, 2002, pp. 301-595.
Synthes Catalog, 2004, 700 sheets.
Synthes Veterinary Brochure, Feb. 2004, 12 sheets.
Taljanovic et al., "Fracture Fixation", RadioGrafics, vol. 23, No. 6, 2003, pp. 1569-1590.
Tornkvist et al., "The strength of plate fixation in relation to the number and spacing of bone screws", Journal of Orthopaedic Trauma, vol. 10, Issue 3, Apr. 1996, 14 sheets.
Veterinary Orthopedic Implants, Inc., "Veterinary Orthopedic Implants Bone Plating Set advertisement", ACVS Veterinary Surgery Medical Journal, vol. 33, No. 1, Jan.-Feb. 2004, 2 sheets.
Veterinary Orthopedic Implants, Inc., "Veterinary Orthopedic Implants TPLO Plates advertisement", ACVS Veterinary Surgery Medical Journal, vol. 34, No. 4, Jul.-Aug. 2005, 2 sheets.
Veterinary Orthopedic Implants. Inc.. "Veterinary Orthopedic Implants Y Plates advertisement", ACVS Veterinary Surgery Medical Journal, vol. 34, No. 6, Nov.-Dec. 2005, 2 sheets.
Veterinary Orthopedic Implants, Inc., "Veterinary Orthopedic Implants 2006 Catalog", Veterinary Orthopedic Implants, Inc., 2006, 226 sheets.
Wheeler et al., "In Vitro Effects of Osteotomy Angle and Osteotomy Reduction on Tibial Angulation and Rotation During the Tibial Plateau-Leveling Osteotomy Procedure", Veterinary Surgery, vol. 32, 2003, pp. 371-377.
Zimmer, Inc., Warsaw, Ind., Brochures "Zimmer Periarticular Distal Radial Locking Plates Surgical Technique", "Zimmer Periarticular Proximal Humeral Locking Plate Surgical Technique", "Zimmer Periarticular Distal Femoral Locking Plate Surgical Technique", "Zimmer Periarticular Proximal Tibial Locking Plate", "Zimmer Periarticular Distal Tibial Locking Plate", "Zimmer Periarticular Radial Styloid Locking Plate", Copyright 2005, 135 sheets.
Begue et al., "Small Fragment Set", Stryker Plating System, No. 982181, Switzerland, 2004, 20 sheets.
Bruecker et al., "AOVET North America Course—Advanced Techniques in Small Animal Fracture Management", Lecture Abstract Manual, Hilton Columbus at Easton Hotel, Columbus, Ohio, Apr. 7-10, 2016, 322 sheets.
Conkling et al., "Comparison of Tibial Plateau Angle Changes after Tibial Plateau Leveling Osteotomy Fixation with Conventional or Locking Screw Technology", Veterinary Surgery, vol. 39, 2010, pp. 475-481.
Degner, "Tibial Plateau Leveling Osteotomy—TPLO", VetSurgery Central, 2006, 8 sheets.
Dejardin, "Tibial Plateau Leveling Osteotomy", Textbook of Small Animal Surgery/ [edited by] Douglas Slatter—3rd ed., Saunders, USA, 2003, pp. 2133-2143.
Gretchen, "Meniscal Injures", Veterinary Clinics of North America: Small Animal Practice, vol. 23, No. 4, Jul. 1993, pp. 831-843.
Gruen et al., "Small Fragment Set: Operative Technique", Stryker Plating System, No. LTSFST Rev. 1, USA, 2004, 20 sheets.
Kyon, "Tibial Plateau Leveling Osteotomy", KYON Veterinary Surgical Products, USA, Sep. 2015, 4 sheets.
Pozzi et al., "Effect of Medical Meniscal Release on Tibial Translation After Tibial Plateau Leveling Osteotomy", Veterinary Surgery, vol. 35, 2006, pp. 486-494.
Slone et al., "Orthopedic Fixation Devices", RadioGraphics, vol. 11, No. 5, Sep. 1991, 25 pp. 823-847.
Slocum et al., "Tibial Plateau Leveling Osteotomy for Repair of Cranial Cruciate Ligament Rupture in the Canine", Veterinary Clinics of North America: Small Animal Practice, vol. 23, No. 4, Jul. 1993, pp. 777-795.
Warzee et al., "Effect of Tibial Plateau Leveling on Cranial and Caudal Tibial Thrusts in Canine Cranial Cruciate-Deficient Stifles: An In Vitro Experimental Study", Veterinary Surgery, vol. 30, 2001, pp. 278-286.

* cited by examiner

FIG. 1
FIG. 2
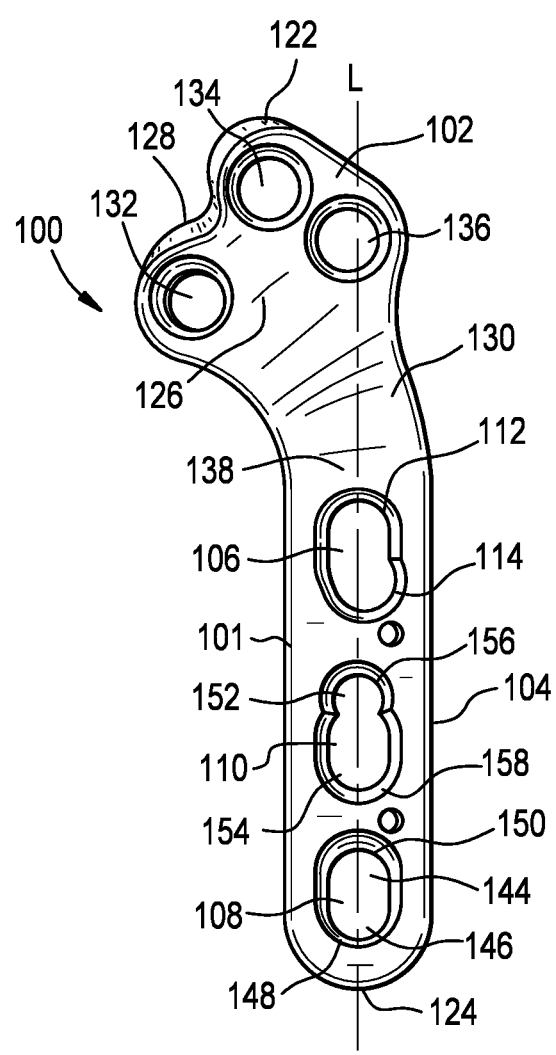
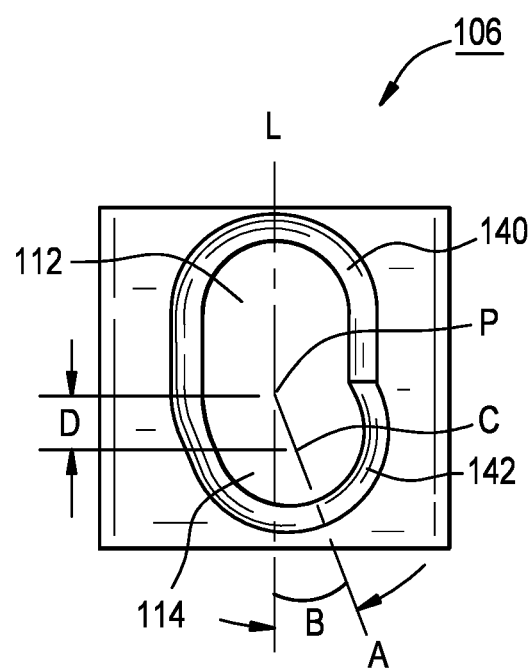

OFFSET HOLE FOR TPLO COMPRESSION

BACKGROUND

A Tibial Plateau Leveling Osteotomy (TPLO) is a surgical procedure for stabilizing a canine stifle joint, which is comparable to a human knee joint, after a ruptured cranial cruciate ligament (CCL). When the CCL is ruptured or torn, the animal's tibia slides forward with respect to its femur, making it difficult to walk and causing pain. In order to stabilize the joint, a curvilinear cut is made to the upper portion of the tibia. This cut portion of the tibia is then rotated to create a more level plane or surface on the top of the tibia, on which the femur can rest. The cut and repositioned portion of the tibia is then secured to the lower portion of the tibia using a TPLO plate.

TPLO plates are generally sized and shaped to extend along the two portions of the tibia to facilitate healing of the tibia in its new configuration. In some cases, however, where the cut portion is not properly seated on the lower portion of the tibia or where the osteotomy cut is not sufficiently compressed against the lower portion of the tibia, the bone may fail to heal properly.

SUMMARY OF THE INVENTION

The present disclosure relates to a Tibial Plateau Leveling Osteotomy (TPLO) plate for providing a cranial and a distal compression of an osteotomy cut. The TPLO plates includes a body extending longitudinally from a proximal end to a distal end and defined via a first surface which, in an operative configuration, faces away from a bone and a second surface which, in the operative configuration, faces toward the bone, the body including a proximal portion configured to be positioned over a cut and repositioned proximal segment of a tibia during a TPLO procedure and a distal portion extending along a longitudinal axis and configured to be positioned over a distal segment of the tibia during the TPLO procedure.

The TPLO plate also includes a first distal hole extending through a proximal end of the distal portion of the body from the first surface to the second surface. The first distal hole includes an elongated portion and an offset portion open to and in communication with one another. The elongated portion extends along the longitudinal axis and an offset portion extending distally from the elongated portion along an offset axis, which extends at an angle relative to the longitudinal axis.

In addition, the TPLO plate includes a second distal hole extending through the distal portion of the body distally of the first distal hole from the first surface to the second surface. The second distal hole extends along the longitudinal axis in alignment with the elongated portion of the first distal hole and including a sloped compression surface along a distal portion thereof. The first distal hole is configured such that when a first distal compression to the osteotomy cut is applied via insertion of a bone fixation element into a distal portion of the second distal hole, the bone fixation element translates along the offset axis from a central axis to a point of intersection to provide a cranial compression to the osteotomy cut.

In an embodiment, a distance between a central axis of the offset portion of the first distal hole along which the bone fixation element is configured to be inserted and a point of intersection of the longitudinal axis and the offset axis is selected so that during the first distal compression, the bone fixation element received along the central axis is configured to move proximally along the offset axis from the central axis to the point of intersection.

In an embodiment, an angle between the longitudinal axis along which the elongated portion extends and the offset axis A along which the offset portion extends corresponds to a desired cranial displacement.

In an embodiment, the TPLO plate further includes a third distal hole extending through the distal portion of the body, between the first and second holes, from the first surface to the second surface and extending along the longitudinal axis, a distal portion of the third distal hole including a sloped compression surface.

In an embodiment, the third distal hole is configured as a combi-hole including a proximal portion configured as a locking hole and a distal portion configured as a dynamic compression hole, the proximal and distal portions of the combi-hole open to and in communication with one another.

In an embodiment, when a second distal compression is provided via the third distal hole, the bone fixation element received within the first distal hole translated proximally along the elongated portion of the first distal hole.

In an embodiment, the second distal hole is configured as a dynamic compression hole including the sloped compression surface.

In an embodiment, the proximal portion of the body includes three proximal holes, each of which extends through the proximal portion, from the first surface to the second surface, along a proximal edge thereof, each of the proximal holes being configured to receive a proximal bone fixation element therein.

In an embodiment, a first one of the three proximal holes extends through the proximal portion in a position configured to facilitate insertion of a first one of the proximal bone fixation elements therethrough into a caudal portion of the proximal segment of the tibia. A second one of the proximal holes extends through the proximal portion in a position configured to facilitate insertion of a second one of the proximal bone fixation elements therethrough into a proximal portion of the proximal segment of the tibia. A third one of the proximal holes extends through the proximal portion in a position configured to facilitate insertion of a third one of the proximal bone fixation elements therethrough into a cranial portion of the proximal segment of the tibia.

In addition, the present disclosure relates to a Tibial Plateau Leveling Osteotomy (TPLO) plate for providing a cranial and a distal compression of an osteotomy cut. The TPLO plate includes a body extending longitudinally from a proximal end to a distal end and defined via a first surface which, in an operative configuration, faces away from a bone and a second surface which, in the operative configuration, faces toward the bone. The body includes a proximal portion configured to be positioned over a cut and repositioned proximal segment of a tibia during a TPLO procedure and a distal portion extending along a longitudinal axis and configured to be positioned over a distal segment of the tibia during the TPLO procedure.

In addition, the TPLO plate includes a first distal hole extending through the distal portion of the body, proximate the distal end thereof, from the first surface to the second surface, the first distal hole including an elongated portion and an offset portion open to and in communication with one another. The elongated portion extends along the longitudinal axis and an offset portion extending distally from the elongated portion along an offset axis, which extends at an angle relative to the longitudinal axis.

Furthermore, the TPLO plate includes a second distal hole extending through the distal portion of the body proximally of the first distal hole from the first surface to the second surface, the second distal hole extending along the longitudinal axis in alignment with the elongated portion of the first distal hole and including a sloped compression surface along a distal portion thereof. The first distal hole is configured such that when a first distal compression to the osteotomy cut is applied via insertion of a bone fixation element into a distal portion of the second distal hole, the bone fixation element translates along the offset axis from a central axis to a point of intersection to provide a cranial compression and a first distal compression to the osteotomy cut.

In an embodiment, the plate further includes a third distal hole extending through the distal portion of the body, between the first hole and the second hole, from the first surface to the second surface and extending along the longitudinal axis, a distal portion of the third distal hole including a sloped compression surface.

Furthermore, the present disclosure relates to a method for a Tibial Plateau Leveling Osteotomy (TPLO). The method includes positioning a bone plate in a desired initial position with a first surface of the bone plate facing away from a tibia and a second surface thereof facing a tibia so that a proximal portion of the bone plate extends over a proximal tibial segment and a distal portion of the bone plate extends over a distal tibial segment that has been cut away from the proximal tibial segment and rotated and seated within a recess formed in the distal tibial segment when the proximal tibia segment was cut away; inserting a first distal bone fixation element into the distal tibial segment of the tibia along a central axis of an offset portion of a first distal hole, which includes an elongated portion extending along a longitudinal axis of the distal portion of the bone plate and the offset portion extending distally from the elongated portion along an offset axis extending at an angle relative to the longitudinal axis; and inserting a second distal bone fixation element into the distal tibial segment via a second distal hole extending through the distal portion of the bone plate distally of the first distal hole so that a head portion of the second distal bone fixation element slides along a sloped compression surface extending along a distal portion of the second distal hole to move the bone plate distally relative to the second distal bone fixation element and provide a first distal compression between the cut and rotated proximal tibial segment, the first distal bone fixation element translating proximally along the offset axis during the first distal compression so that the bone plate rotates about the second distal bone fixation element and the proximal portion of the bone plate is moved in a cranial direction to provide a cranial compression of the proximal tibial segment against the distal tibial segment.

In an embodiment, the second distal hole extends long the longitudinal axis, in alignment with the elongated portion of the first distal hole.

In an embodiment, during the cranial compression, the first distal bone fixation element translates along the offset axis from the central axis to a point at which the longitudinal axis and the offset axis intersect.

In an embodiment, the method further includes inserting a third distal bone fixation element into the distal tibial segment via a third distal hole extending through the distal portion of the bone plate between the first and second distal holes so a head portion of the second distal bone fixation element slides along a sloped compression surface extending along a distal portion of the third distal hole of the third distal hole to move the bone plate distally relative to the third distal bone fixation element and provide a second distal compression between the cut and rotated proximal tibial segment and the distal tibial segment.

In an embodiment, the first distal bone fixation element translates proximally along the elongated portion of the first distal hole.

In an embodiment, the third distal bone fixation element extends along the longitudinal axis, in alignment with the second distal hole and the elongated portion of the first distal hole.

In an embodiment, the method further includes inserting a first proximal bone fixation element through a first proximal hole and a second proximal bone fixation element through a second proximal hole into the proximal tibia segment, the first and second proximal holes extending through the proximal portion of the bone plate so that, when the bone plate is in the desired initial position, the first and second proximal bone fixation elements fix the proximal portion of the bone plate relative to the proximal tibial segment prior to insertion of the second distal bone fixation element through the second distal hole.

In an embodiment, the first proximal bone fixation element is inserted into a cranial side of the proximal tibial segment.

BRIEF DESCRIPTION

FIG. 1 shows a plan view of a TPLO bone plate according to an exemplary embodiment of the present disclosure;

FIG. 2 shows an enlarged plan view of a first hole extending through a distal portion of the TPLO plate of FIG. 1;

DETAILED DESCRIPTION

Figure 3:
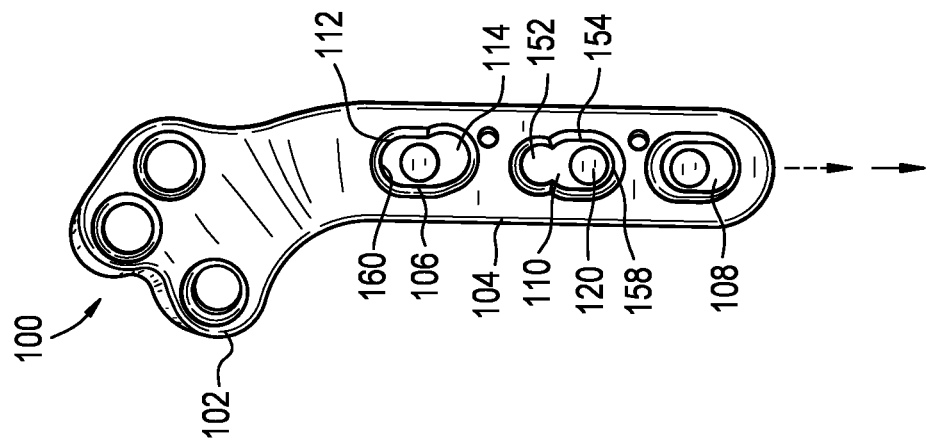
FIG. 3 shows a plan view of the TPLO plate of FIG. 1, with a first a bone fixation element and a second bone fixation element inserted into an offset portion of the first hole and a second hole, respectively.

The present disclosure may be further understood with reference to the following description and the appended drawings, wherein like elements are referred to with the same reference numerals. The present disclosure relates to a Tibial Plateau Leveling Osteotomy (TPLO) plate and, in particular, relates to a TPLO plate configured to provide both cranial (i.e., transverse) and distal (i.e., axial) compression during a TPLO procedure. Exemplary embodiments of the present disclosure describe a TPLO plate comprising a proximal portion configured to be positioned over a cut and repositioned upper portion (e.g., proximal portion) of a tibia, and a distal portion configured to be positioned along a lower portion (e.g., distal portion) of the tibia.

The distal portion of the plate includes three holes positioned along the length of the distal portion so that bone fixation members inserted into these holes work in concert to provide both cranial and distal compression of the interface between the cut and repositioned portion of the tibia and the lower portion of the tibia. The first hole includes an elongated portion extending along a longitudinal axis of the distal portion of the plate and an offset portion that extends distally therefrom, along an offset axis angled with respect to the longitudinal axis.

A surface (i.e., a side wall) of the offset portion of the first hole meets a surface (i.e., a side wall) of the elongated portion of the first hole at an angle. In an embodiment, the second hole is elongated along the longitudinal axis and is distal of the first hole so that, when a first bone fixation element is inserted through the offset portion of the first hole into the bone and a second bone fixation element is inserted into the bone via the second hole, sliding the plate distally relative to the first and second bone fixation elements, moves the plate distally while the proximal portion of the plate is rotated due to the angulation of the offset axis until the first bone fixation element enters the elongated portion of the first hole. As the plate is moved so that distally from this point, no further rotation of the plate occurs. The angulation of the offset axis with respect to the longitudinal axis is selected so that the rotation of the plate as the first bone fixation element traverses the offset portion moves the proximal portion of the plate (and the cut and rotated section of bone coupled thereto) relative to the lower portion of the tibia to provide cranial compression at the interface between the cut portion of bone and the lower tibia while movement of the plate distally relative to the first and second bone fixation elements moves the proximal portion of the plate distally to apply a first distal compression across the osteotomy cut.

The distal portion of the plate further includes a third hole extending therethrough, between the first and second holes. The third hole is configured so that, when engaged via a third bone fixation element inserted therethrough, the plate is moved distally relative to the tibia so that the position of the first bone fixation element within the elongated portion of the first hole is increasingly proximal, and a second distal compression is provided across the osteotomy cut.

It will be understood by those of skill in the art that although the TPLO plates of the present embodiments are described with respect to a canine CCL, the TPLO plate of the present disclosure may also be used to treat the tibias of other quadrupeds such as, for example, felines, bovines, equines, etc. It will also be understood by those of skill in the art that the terms proximal, distal, caudal, and cranial, as used herein, are anatomical directional terms for an animal such as, for example, a canine and are employed in a manner consistent with their standard anatomical meanings. In particular, the term proximal refers to a direction toward a center of the body while distal refers to a direction away from the center of the body while cranial refers to a direction toward a head of the animal and caudal refers to a direction away from the head.

As shown in FIGS. 1-5, a TPLO plate 100 according to an exemplary embodiment of the present disclosure is configured to secure proximal and distal segments of a tibia which have been separated from one another during a TPLO procedure via a substantially curvilinear osteotomy cut as would be understood by those skilled in the art. During a TPLO procedure, a proximal segment of the tibia is cut away from the rest of the tibia, rotated relative to the tibia to a new position selected to enhance the stability of, for example, a canine stifle joint (e.g., after injury to a cranial cruciate ligament (CCL)), and secured to the distal segment in this desired position—e.g., via a bone plate coupled to the cut segment of the tibia and the distal segment of the tibia.

According to an exemplary embodiment, the plate 100 comprises a body 101 including a proximal portion 102 sized and shaped to be positioned over and coupled to the cut and repositioned proximal segment of the tibia, and a distal portion 104 sized and shaped to extend along and be coupled to the distal segment of the tibia so that the plate 100 fixes the position of the cut and repositioned portion of the tibia relative to the distal segment. In an exemplary embodiment the distal portion 104 includes at least three holes—a first hole 106, a second hole 108, and a third hole 110—extending therethrough.

Those skilled in the art will understand that additional holes may be added as desired so long as they do not impede the functioning of the plate 100 with respect to the distal and cranial compression as will be described below. The first hole 106 includes an elongated portion 112 extending along a longitudinal axis L of the plate 100 and an offset portion 114 extending distally from the elongated portion 112 along an offset axis A that is angled with respect to the longitudinal axis L. As will be described in further detail below, the offset portion 114 of the first hole 106 and the second hole 108 are configured to work together so that, when first and second bone fixation elements 116, 118 are inserted therein, respectively, desired levels of distal and cranial compression of the osteotomy cut are provided at the interface between the cut and repositioned portion of the bone and the distal segment of the tibia.

The elongated portion 112 of the first hole 106, the second hole and the third hole 110 are configured to work together so that, when a third bone fixation element 120 is subsequently inserted into the third hole 110, a desired amount of additional distal compression is provided. The amounts of cranial and distal compression are selected to ensure that the cut and repositioned proximal segment of the tibia is seated within a recessed portion of the distal segment formed via the curvilinear cut to optimize healing of the bone.

As shown in FIG. 1, the plate 100 includes a body 101 extending longitudinally from a proximal end 122 to a distal end 124. The body 101 is defined via a first surface 126 which, in an operative configuration, faces away from a bone (e.g., the tibia), and a second surface 128 which, in the operative configuration, faces toward the bone. The body 101 includes the proximal portion 102 and the distal portion 104, which are connected to one another via a neck portion 130 so that, when in the operative configuration, the proximal portion 102 is positioned over and coupled to the proximal segment of the tibia, as desired, and the distal portion 104 extends over and is coupled to the distal segment of the tibia, the neck portion 130 extends across the interface between the cut-away portion of the proximal tibia and the distal tibia at the curvilinear osteotomy cut.

The distal portion 104 extends distally of the proximal portion 102 along the longitudinal axis L. According to an exemplary embodiment, the neck portion 130 of one embodiment is curved so that the proximal portion 102 is offset (e.g., angled) with respect to the longitudinal axis L along which the distal portion 104 extends. For example, the proximal portion 102 may be angled in a caudal direction relative to the longitudinal axis L although, as would be understood by those of skill in the art, the angle may be selected in any manner desired to conform to the geometry of the cut-away and rotated portion of the tibia relative to the distal tibia (or any other bone segment involved) in any given procedure.

As will be understood by those of skill in the art, the proximal portion 102 is, in this embodiment, preferably constructed, sized, shaped, and contoured to conform to the shape and orientation of the cut-away proximal segment of the tibia when the cut-away segment is in a desired position relative to the distal tibia and the distal portion 104 is in a desired position on the distal tibia. In particular, the second surface 128 of this embodiment is specifically contoured so that, when the proximal portion 102 is positioned over the proximal segment of the tibia, the second surface 128 extends along an exterior surface of the cut and rotated proximal segment of the tibia, in contact therewith.

According to an exemplary embodiment, the proximal portion 102 includes at least three holes—a first hole 132, a second hole 134, and a third hole 136—each of which extends through the proximal portion 102 along a central axis, from the first surface 126 to the second surface 128. The first, second and third holes 132, 134, 136 may be positioned adjacent an edge extending along the proximal end 122 of the plate 100. Each of the first, second and third holes 132, 134, 136 of the proximal portion 102 of this embodiment is configured to receive therein a bone fixation element such as, for example, a locking screw to fix the proximal portion 102 of the plate 100 relative to the cut and rotated proximal segment of the tibia.

In an exemplary embodiment, the first hole 132 is positioned on the plate 100 and oriented so that, when the plate 100 is positioned on a tibia in a desired position, the first hole 132 is positioned to receive a bone fixation element through a caudal portion of the resected proximal segment of the tibia, while the second hole 134 is positioned and oriented to receive a bone fixation element through a proximal portion of the resected proximal segment of the tibia, and the third hole 136 is positioned and oriented on the plate 100 to receive a bone fixation element through a cranial portion of the resected proximal segment of the tibia. As would be understood by those skilled in the art, central axes of each of the first, second and third holes 132, 134, 136 may be optionally angled to direct bone fixation elements inserted therealong into a desired portion of the proximal segment of the bone (e.g., a central mass of the resected portion of the proximal tibia).

Furthermore, any or all of the first, second and third holes 132, 134, 136 of the proximal portion 102 may be configured as locking holes, including a threading extending therein for engaging corresponding threading on the head of a bone fixation element inserted therein. Thus, bone fixation elements inserted therein may be locking screws including corresponding threading along a head portion thereof. It will be understood by those of skill in the art, however, that the first, second and third holes 132, 134, 136 of the proximal portion 102 of the plate 100 may have any of a variety of configurations so long as bone fixation elements are insertable therethrough to be inserted into a desired portion of the bone.

The distal portion 104 of the plate 100 is contoured to extend, when in the desired position, along the distal segment of the tibia. In particular, in the operative configuration, the second surface 128 extends along the distal segment, in contact therewith. As described above, the distal portion 104 of this embodiment also at least includes three holes extending therethrough—the first hole 106, the second hole 108 and the third hole 110. The first hole 106, the second hole 108, and the third hole 110 work in concert to provide desired levels of cranial and distal compression to the osteotomy cut of the tibia.

The first hole 106 is positioned adjacent to a proximal end 138 of the distal portion 104, adjacent to the neck portion 130. The first hole 106 extends through the plate 100 from the first surface 126 to the second surface 128 and includes the elongated portion 112 and the offset portion 114, each of which is configured to receive the first bone fixation element 116 therein. The elongated portion 112 is elongated along the longitudinal axis L while the offset portion 114 extends distally therefrom along the offset axis A, which is angled with respect to the longitudinal axis L. The elongated portion 112 and the offset portion 114 are open to and in communication with one another so that a surface 140 (i.e., a side wall of the elongated portion 112) defining the elongated portion 112 of the first hole 106 meets a surface 142 (i.e., a side wall of the offset portion 114) defining the offset portion 114 at an angle corresponding to an angle B between the longitudinal axis L and the axis A.

In an exemplary embodiment, the offset portion 114 extends distally from the elongated portion 112 angled cranially relative to the longitudinal axis L (i.e., so that the distal end of the offset portion 114 is separated transversely from the axis L on the cranial side of the axis L while the offset axis A, if extended proximally beyond the axis L would extend toward the caudal side. Thus, when the first bone fixation element 116 is received in the offset portion 114 and a second bone fixation element 118 is inserted through the second hole 108 and the plate 100 is moved distally over the first and second bone fixation elements 116, 118, respectively, the first and second bone fixation elements 116, 118 remain stationary (i.e., coupled to the bone) while the plate 100 translates distally so that the first bone fixation element 116 passes proximally along the offset portion 114 while the portion of the plate 100 surrounding the second hole 108 moves distally along the axis L. This rotates the plate 100 so that the proximal end 122 of the plate moves in a cranial direction against the surface of the osteotomy cut in the distal segment of the tibia to apply cranial compression across the osteotomy cut, as will be described in further detail below.

The surfaces 140, 142 defining the first hole 106 are, in this embodiment, configured to correspond to a size of a head portion of the first bone fixation element 116. For example, the surfaces 140, 142 may taper from the first surface 126 toward the second surface 128 and/or may include a curvature corresponding to an underside the head portion (e.g., a surface of the head portion which is configured to engage the first and second surfaces 126, 128) so that upon insertion of the first bone fixation element 116 thereinto, the head portion of the first bone fixation element 116 is slidable along the axes of the elongated portion 112 and the offset portion 114, as will be described in further detail below.

In addition, the first hole 106 of this embodiment is configured with the length of the elongated portion 112 selected so that, when the first bone fixation element was initially positioned as desired, the head portion of the first bone fixation element 116 is, after the final distal compression, seated along the surface 140 to sit flush with the first surface 126 of the plate 100, as will be understood by those of skill in the art. In an exemplary embodiment, the first bone fixation element 116 is, for example, a standard cortex screw.

In an exemplary embodiment, the angle B between the longitudinal axis L and the offset axis A may range from between approximately 10 degrees to 35 degrees. The offset portion 114 of the first hole 106, however, may have any of a variety of configurations and angulations relative to the elongated portion 112 depending on the positions of the first and second holes along the axis L and a desired amount of cranial and distal compression.

As would be understood by those skilled in the art, the angle B is selected based on a desired cranial compression to be provided by the plate 100 for a given amount of distal compression. A distance D between a central axis C of the offset portion 114 along which the first bone fixation element 116 is configured to be inserted and a point of intersection P of the longitudinal axis L and the offset axis A is specifically selected such that a first distal compression achieved via insertion of the second bone fixation element 118 into the second hole 108 will translate the first bone fixation element 116 received along the central axis C proximally along the axis A from this initial position along the central axis C to the point of intersection P.

It will be understood by those or skill in the art that the distance D and the angle B between the axis L and offset axis A may be determined based on any of a number of factors including, for example, a desired cranial and distal compression, and a distance between various holes 106, 108, 110. That is, those skilled in the art will understand the geometric relationships that allow a plate 100 to be designed to provide a desired amount of rotation of the proximal portion of the plate 100 (cranial compression) for a given amount of distal compression.

The second hole 108 extends through the distal portion 104, distally of the first hole 106, and is configured to receive the second bone fixation element 118 therein. In an exemplary embodiment, the second hole 108 extends through the distal portion 104 proximate the distal end 124 and in longitudinal alignment with the elongated portion 112 of the first hole 106. The second hole 108 in this embodiment is configured as a dynamic compression hole configured to provide distal compression across the osteotomy cut. For example, the second hole 108 of this embodiment extends through the distal portion 104 from the first surface 126 to the second surface 128 and is elongated along the longitudinal axis L, in alignment with the elongated portion 112 of the first hole 106. The second hole 108 includes a proximal portion 144 and a distal portion 146, which facilitates translational movement of second hole 108 relative to the second bone fixation element 118 that is received therein so that the second bone fixation element traverses from the distal portion 146 toward the proximal portion 144, as a first distal compression is applied to the tibia.

The distal portion 146 of the second hole 108 includes a sloped compression surface 148 inclined at a curve/angle selected so that, as an underside of a head portion of the second bone fixation element 118 is pressed thereagainst (e.g., as the third bone fixation element 120 is inserted gradually further into the bone and further through the plate 100), the sloped compression surface 148 slides along the head portion of the second bone fixation element 118. In particular, as the second bone fixation element 118 is driven more deeply into the bone, the head portion of the second bone fixation element 118 slides along the sloped compression surface 148 moving the plate 100 distally relative to the second bone fixation element 118, thereby applying distal compression across the osteotomy—i.e., pulling the proximal segment of the tibia distally against the distal segment of the tibia as the proximal portion 102 of the plate 100, which is coupled to the cut-away proximal segment of the tibia, is drawn distally by the movement of the distal portion of the plate 100.

According to an exemplary embodiment, the proximal portion 144 of the second hole 108 is defined via a surface 150 sized, shaped, and configured to correspond to the size and shape of an underside of the second bone fixation element 118 which, in one embodiment, is a cortex screw. In an exemplary embodiment, the surface 150 may be tapered and/or curved from the first surface 126 toward the second surface 128 and, in one example, is configured as a spherical relief configured to seat the head portion of the second bone fixation element 118 therein so that the head portion of the second bone fixation element 118 is substantially flush with the first surface 126 of the body 101 of the plate 100 as would be understood by those skilled in the art. It will also be understood by those of skill in the art, however, that the head portion of the second bone fixation element 118 is not required to be finally seated within the spherical relief as the plate 100 moves so that the second bone fixation element 118 passes from the distal portion 146 toward the proximal portion 144 via a distance corresponding to a desired axial compression.

As discussed above, the offset portion 114 of the first hole 106 and the second hole 108 work in concert so that, when the first bone fixation element 116 and the second bone fixation element 118 are inserted into respective ones of the first and second holes 106, 108, cranial compression is applied to the osteotomy cut. In particular, the first bone fixation element 116 may be inserted into the offset portion 114 along the central axis C thereof and the second bone fixation element 118 is subsequently inserted into the distal portion 146 of the second hole 108 so that the head portion of the second bone fixation element 118 with the sloped compression surface 148 moves the plate 100 distally relative to the second bone fixation element 118. This first distal compression is applied until the plate 100 has moved so that the first bone fixation element 116 has translated along the offset axis A from the central axis C to the point of intersection P, where the longitudinal axis L of the elongated portion 112 of the first hole 106 and the offset axis A of the offset portion 114 intersect.

Figure 4:
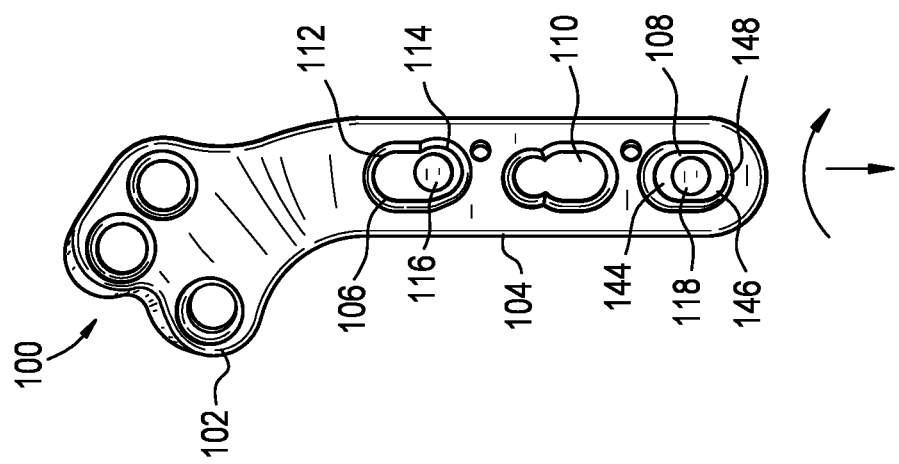
FIG. 4 shows a plan view of the TPLO plate of FIG. 1, after a first distal compression and a cranial compression.
Figure 5:
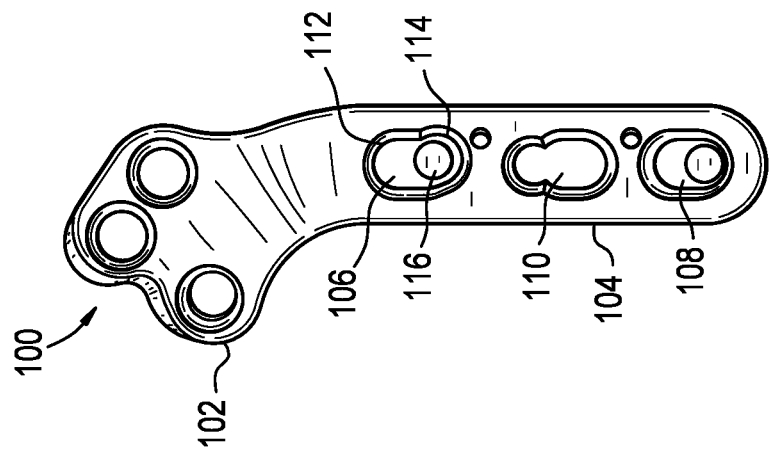
FIG. 5 shows a plan view of the TPLO plate of FIG. 1, after a second distal compression.

Further insertion of the second bone fixation element 118 into the bone translates the first bone fixation element 116 proximally along the offset axis A as the first bone fixation element 116 interfaces with the surface 142 of the offset portion 114. This causes the plate 100 to rotate about the second bone fixation element 118 (clockwise as seen in FIG. 4) so that the proximal portion 102 of the plate 100, which is coupled to the cut proximal segment of the tibia, moves in a cranial direction, applying a cranial compression across the osteotomy cut. Thus, this portion of the first distal compression simultaneously applies the cranial compression.

The third hole 110, extends through the distal portion 104 in a position extending between the first and second holes 106, 108, and is configured to receive the third bone fixation element 120 therein. In an exemplary embodiment, the third hole 110 extends through the body 101 from the first surface 126 to the second surface 128 along the longitudinal axis L, substantially in alignment with the elongated portion 112 of the first hole 106 and the second hole 108. In one exemplary embodiment, the third hole 110 is configured as a combi-hole including a proximal portion 152 configured to provide locking fixation of the plate 100 relative to the bone and a distal portion 154 configured to provide dynamic compression. The proximal and distal portions 152, 154 are open to and in communication with one another.

The proximal portion 152 in this embodiment is configured as a locking hole extending through the first surface 126 to the second surface 128 along a central axis, which extends perpendicular relative to the longitudinal axis L. In one embodiment, the central axis of the proximal portion 152 extends substantially perpendicular to the longitudinal axis L. It will be understood by those of skill in the art, however, that the central axis of the proximal portion 152 may be non-perpendicularly angled relative to the central axis of the proximal portion 152 so that a bone fixation element inserted therealong may be inserted into a desired portion of a bone offset from the portion immediately beneath the axis L. A surface 156 defining the proximal portion 152 may include a threading extending therealong for engaging a corresponding threading along a head of, for example a locking screw, to provide a locking fixation between the plate and the bone.

Similarly to the second hole 108, the distal portion 154 in this embodiment includes a sloped compression surface 158 inclined at a curve/angle selected so that, as an underside of a head portion of the third bone fixation element 120 is pressed thereagainst (e.g., as the third bone fixation element 120 is inserted gradually further into the bone and further through the distal portion 154), the sloped compression surface 158 slides along the head portion of the third bone fixation element 120. As the third bone fixation element 120 is driven further into the bone, the head portion of the third bone fixation element 120 slides along the sloped compression surface 158 moving the plate 100 distally relative to the third bone fixation element 120. In this embodiment, the third bone fixation element 120 is a standard cortex screw.

As discussed above, the elongated portion 112 of the first hole 106 and the third hole 110 work in concert so that, when the third bone fixation element 120 is subsequently inserted into the distal portion 154 of the third hole 110, the head portion of the third bone fixation element 120 slides along the sloped compression surface 158 providing a second distal compression across the osteotomy cut, drawing the cut proximal segment of the tibia which is coupled to the proximal portion 102 of the plate, further distally against the distal segment of the tibia. As the plate 100 is moved distally relative to the third bone fixation element 120, the first bone fixation element 116 translates proximally along the elongated portion 112 of the first hole 106.

According to an exemplary method, the plate 100 may be used to provide desired amounts of both cranial and distal compression during a TPLO procedure. As will be understood by those of skill in the art, upon cutting of a proximal segment of a tibia from a distal segment of the tibia via a substantially curvilinear osteotomy cut, the proximal segment is rotated and repositioned relative to the distal segment and the plate 100 is then placed over the separated bone segments so that the proximal portion 102 is positioned over the cut and repositioned proximal segment of the tibia in a desired alignment and the distal portion 104 is positioned over a target portion of the distal segment of the tibia.

According to an exemplary method, the first bone fixation element 116 is inserted along the central axis C of the offset portion 114 of the first hole 106 and the second bone fixation element 118 is inserted through the distal portion 146 of the second hole 108 to establish a preliminary position of the plate 100 relative to the tibia so that the proximal portion 102 of the body 101 of the plate 100 is positioned over the cut proximal segment of the tibia and the distal portion 104 is positioned over the distal segment of the tibia. Once the preliminary position has been established, bone fixation elements may be inserted through at least two of the holes extending through the proximal portion 102 of the plate 100 to fix the proximal portion 102 relative to the proximal segment of the tibia. In one embodiment, bone fixation elements are inserted through a cranial one of the holes (e.g., third hole 136) and one of the other holes (e.g., the first hole 132 and the second hole 134) of the proximal portion 102.

The second bone fixation element 118 may then be tightened (e.g., rotatably inserted further into the distal portion 146 of the second hole 108 so that the head portion of the second bone fixation element 118 engages the compression surface 148 thereof, causing the plate 100 to be moved distally with respect to the second bone fixation element 118 to apply a first distal compression to the osteotomy cut—i.e., by moving the proximal segment of the tibia distally toward the distal segment of the tibia. As the plate 100 is being moved distally with respect the second bone fixation element 118 (i.e., the second bone fixation element 118 is translated from the distal portion 146 toward the proximal portion 144 of the second hole 108), the first bone fixation element 116 also translates along the offset axis A of the offset portion 114 of the first hole 106, rotating the plate 100 about the second bone fixation element 118 and providing a simultaneous cranial compression in which the proximal portion 102 of the plate 100 is moved in a cranial direction.

In particular, as the plate 100 moves so that the first bone fixation element 116 translates proximally along the offset axis A, the first bone fixation element 116 interfaces with a portion of the surface 142, which forces the proximal portion 102 of the plate 100 in the cranial direction.

As described above, the movement of the plate 100 generating the first distal compression moves the plate relative to the first bone fixation element 116 so that the first bone fixation element 116 translates from its insertion position along the central axis C to the point P at which the longitudinal axis L of the elongated portion 112 intersects the offset axis A. The third bone fixation element 120 may then be inserted into the distal portion 154 so that the head portion of the third bone fixation element 120 engages the compression surface 158 thereof, moving the plate 100 further distally with respect to the distal segment of the tibia to apply a second distal compression across the osteotomy cut. During the second distal compression the plate 100 moves so that the third bone fixation element 120 translates from the distal portion 154 toward the proximal portion 152 of the third hole 110 and the first bone fixation element 116 translates from the point P along the longitudinal axis L of the elongated portion 112 of the first hole 106 toward a proximal end 160 thereof.

Upon completion of the cranial and distal compression, the first bone fixation element 116 is tightened to fix the distal portion 104 of the plate 100 relative to the distal segment of the tibia. Additional bone fixation elements may be inserted through any remaining holes extending through to provide final fixation as desired. For example, bone fixation elements may be inserted through any remaining holes 132, 134, 136 of the proximal portion 102, to provide further locking of the plate 100 in the desired position relative to the tibia.

Figure 6:
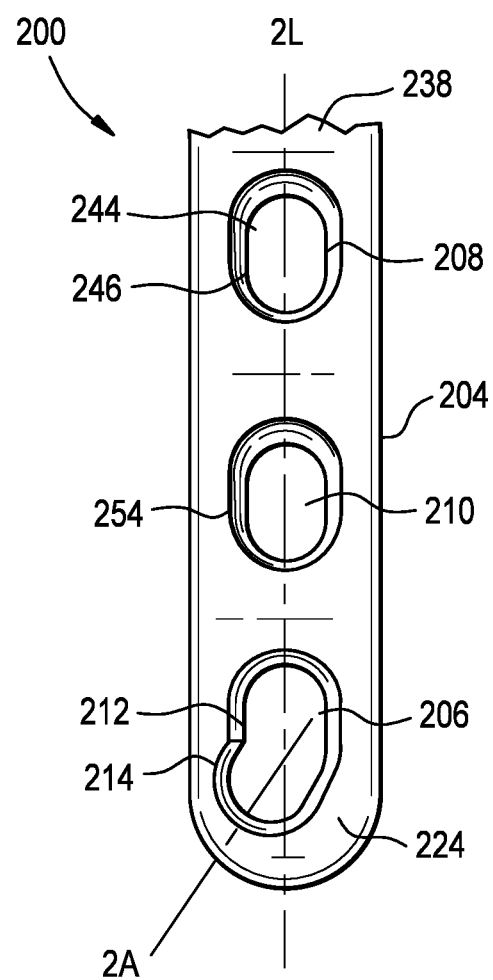
FIG. 6 shows a plan view of a TPLO bone plate according to another exemplary embodiment of the present disclosure.

Except as detailed below, a TPLO plate 200 according to another exemplary embodiment shown in FIG. 6, is substantially similar to the plate 100, as described above, comprising a proximal portion (not shown) and a distal portion 204 configured to fix a proximal segment of a tibia relative to a distal segment of the tibia, respectively, during a TPLO procedure. The proximal portion is substantially similar to the proximal portion 102 of the plate 100 and is sized and shaped to be positioned over and coupled to the proximal segment of the tibia, which is cut away from the distal segment and repositioned relative thereto. The distal portion 204 is sized and shaped to extend along and be coupled to the distal segment (i.e., the shaft) of the tibia so that the plate 200 fixes the position of the cut and repositioned portion of the tibia relative to the distal segment. Similarly to the plate 100, the distal portion 204, includes at least three holes—a first hole 206, a second hole 208, and a third hole 210, configured to work together to provide distal and cranial compression across the osteotomy cut and ensure that the cut and repositioned proximal segment of the tibia is optimally seated within a recessed portion of the distal segment formed via the osteotomy cut.

Similarly to the first hole 106, the first hole 206 includes an elongated portion 212 extending along a longitudinal axis 2L of the plate 200 (along which the distal portion 204 extends) and an offset portion 214 extending distally from the elongated portion 212 along an offset axis A angled with respect to the longitudinal axis L. The offset portion 214 of the first hole 206 and the second hole 208 are configured to work together so that, when first and second bone fixation elements are inserted therein, respectively, desired levels of distal and cranial compression of the osteotomy cut are provided at the interface between the cut and repositioned portion of the bone and the distal segment of the tibia. The elongated portion 212 of the first hole 206, the second hole and the third hole 210 are configured to work together so that, when a third bone fixation element is subsequently inserted into the third hole 210, a desired amount of additional distal compression is provided.

As will be described in further detail below, however, a position of the first and second holes 206, 208 along the distal portion 204 is transposed relative to the plate 100, and an offset portion 214 of the first hole 206 extends distally from an elongated portion 212 of the first hole 206 at an angle extending in a caudal direction—i.e., so that the first hole 206 is a mirror image of the first hole 106 relative to the longitudinal axis 2L.

The first hole 206, in this embodiment, is positioned adjacent to a distal end 224 of the distal portion 204. Similarly to the first hole 106, the first hole 206 extends through the distal portion 204 and includes the elongated portion 212 and the offset portion 214, which are open to one another. The elongated portion 212 extends along the longitudinal axis 2L while the offset portion 214 extends distally from the elongated portion 212, along an offset axis 2A angled with respect to the longitudinal axis 2L. As discussed above, the first hole 206 is substantially similar to the first hole 106, as described above with respect to the plate 100, except that the first hole 206 is a mirror image of the first hole 106, as described above with respect to the plate 100, relative to the longitudinal axis 2L. In particular, the offset portion 214 extends distally from the elongated portion 212, angled caudally relative to the longitudinal axis 2L (i.e., so that the distal end of the offset portion is separated transversely from the axis 2L on a caudal side of the axis 2L while the offset axis 2A, if extends proximally beyond the axis 2L would extend toward a cranial side).

As will be described in further detail below, when a first bone fixation element is received within the offset portion 214 and the plate 200 is moved in distally relative to the first bone fixation element, the first bone fixation element moves through the offset portion 214, rotating of the plate 200 so that the distal end 224 of the plate 200 is moved in a caudal direction and a proximal end of the plate is moved in a cranial direction to apply a cranial compression across the osteotomy cut.

The second hole 208 is substantially similar to the second hole 108 described with respect to the plate 100. The second hole 208, however, extends through the distal portion 204 proximally of the first hole 206 and, in one exemplary embodiment, is positioned proximate a proximal end 238 of the distal portion 204. Similarly to the second hole 108, the second hole 208 extends through the distal portion 204 in longitudinal alignment with the elongated portion 212 of the first hole 206 and, in this embodiment, is configured as a dynamic compression hole.

In particular, the second hole 208 includes a proximal portion 244 and a distal portion 246 which includes a sloped compression surface facilitating translational movement of the second hole 208 relative to a second bone fixation element received therein, so that the second bone fixation element traverses from the distal portion 246 toward the proximal portion 244, a first distal compression is applied to the tibia. As the second bone fixation element is driven into the bone, a head portion thereof slides along the sloped compression surface of the distal portion 246 of the second hole 208, moving the plate 200 distally relative to the second bone fixation element so that a distal compression is applied across the osteotomy.

Similarly to the plate 100, the offset portion 214 of the first hole 206 and the second hole 208 work in concert so that, when the first bone fixation element and the second bone fixation element are inserted into respective ones of the first and second holes 206, 208, cranial compression is applied to the osteotomy cut. In particular, the first bone fixation element may be inserted into the offset portion 214 and the second bone fixation element subsequently inserted into the distal portion 246 of the second hole 208 so that the head portion of the second bone fixation element engages the sloped compression surface of the distal portion 246 to move the plate 200 distally relative to the second bone fixation element.

This first distal compression is applied until the plate 200 has moved so that the first bone fixation element has translated along the offset axis 2A to a point where the longitudinal axis 2L and the offset axis 2A intersect. Since the offset axis 2A is angled with respect to the longitudinal axis 2L, the distal translation of the plate 200 relative to first bone fixation element rotates the plate 200 about the second bone fixation element such that the distal end 224 of the plate 200 moves in a caudal direction while the proximal end of the plate 200 moves in a cranial direction. Thus, the proximal portion of the plate 200, which is coupled to the proximal segment of the tibia, moves in the cranial direction, applying a cranial compression across the osteotomy cut. Accordingly, the first distal compression achieved via the insertion of the second bone fixation element into the second hole 208 applies a simultaneous cranial compression.

The third hole 210 is substantially similar to the third hole 110, described above with respect to the plate 100. In particular, the third hole 210 extends through distal portion 204 in a position extending between the first and second holes 206, 208, in longitudinal alignment therewith. In one embodiment, the third hole 208 is configured as a combihole. A distal portion 254 of the third hole 208 is configured to provide dynamic compression and may include a sloped compression surface. Thus, after achieving a cranial compression and a first level of distal compression via the insertion of the first and second bone fixation elements through the offset portion 214 of the first hole 206 and the distal portion 246 of the second hole 208, a third bone fixation element may be inserted through the distal portion 254 to provide a second distal compression.

As discussed above, the elongated portion 212 of the first hole 206 and the third hole 210 work in concert so that, when the third bone fixation element is subsequently inserted into the distal portion 254 of the third hole 210, the head portion of the third bone fixation element slides along the sloped compression surface of the distal portion 254 to move the plate 200 distally relative to the third bone fixation element. As the plate 200 is moved distally relative to the third bone fixation element, the first bone fixation element received within the first hole 206 translates proximally (relative to the plate 200) along the elongated portion 212 of the first hole 206. Thus, the cut proximal segment of the tibia, which is coupled to the proximal portion of the plate 200, is drawn further distally against the distal segment of the tibia.

As will be understood by those of skill in the art, the plate 200 may be used in a manner substantially similar to the plate 100 to provide both a cranial and a distal compression to an osteotomy cut. As described above, the first bone fixation element will be inserted through the offset portion 214 of the first hole 206 at the distal end 224 of the distal portion 204 of the plate 200. The second bone fixation element will subsequently be inserted through the distal portion 246 of the second hole 208 proximate the proximal end 238 of the distal portion 204 of the plate 200 to provide the first distal compression and the cranial compression. The third bone fixation element may then be inserted through the distal portion 254 of the third hole 210 to provide the second, final distal compression.

It will be understood by those of skill in the art that modifications and variations may be made in the structure and methodology of the present invention, without departing from the spirit and scope of the invention. Thus, it is intended that the present invention cover the modifications and variations of this invention, provided that they come within the scope of the appended claims and their equivalents.

What is claimed is:

1. A Tibial Plateau Leveling Osteotomy (TPLO) plate for providing a cranial and a distal compression of an osteotomy cut, comprising:
   a body extending longitudinally from a proximal end to a distal end and defined via a first surface which, in an operative configuration, faces away from a bone and a second surface which, in the operative configuration, faces toward the bone, the body including a proximal portion configured to be positioned over a cut and repositioned proximal segment of a tibia during a TPLO procedure and a distal portion extending along a longitudinal axis and configured to be positioned over a distal segment of the tibia during the TPLO procedure;
   a first distal hole extending through a proximal end of the distal portion of the body from the first surface to the second surface, the first distal hole including an elongated portion and an offset portion open to and in communication with one another, the elongated portion extending along the longitudinal axis and the offset portion extending distally from the elongated portion along an offset axis, which extends at an angle relative to the longitudinal axis; and
   a second distal hole extending through the distal portion of the body distally of the first distal hole from the first surface to the second surface, the second distal hole extending along the longitudinal axis in alignment with the elongated portion of the first distal hole and including a sloped compression surface along a distal portion thereof,
   wherein the first distal hole is configured such that when a first distal compression to the osteotomy cut is applied via insertion of a bone fixation element into the distal portion of the second distal hole, a second bone fixation element translates along the offset axis from a central axis to a point of intersection to provide a cranial compression to the osteotomy cut.

2. The plate of claim 1, wherein a distance between the central axis of the offset portion of the first distal hole along which the second bone fixation element is configured to be inserted and the point of intersection of the longitudinal axis and the offset axis is selected so that during the first distal compression, the second bone fixation element received along the central axis is configured to move proximally along the offset axis from the central axis to the point of intersection.

3. The plate of claim 1, wherein the angle between the longitudinal axis along which the elongated portion extends and the offset axis along which the offset portion extends corresponds to a desired cranial displacement.

4. The plate of claim 1, further comprising:
   a third distal hole extending through the distal portion of the body, between the first and second distal holes, from the first surface to the second surface and extending along the longitudinal axis, a distal portion of the third distal hole including a sloped compression surface.

5. The plate of claim 4, wherein the third distal hole is configured as a combi-hole including a proximal portion configured as a locking hole and a distal portion configured as a dynamic compression hole, the proximal and distal portions of the combi-hole open to and in communication with one another.

6. The plate of claim 4, wherein when a second distal compression is provided via the third distal hole, the bone fixation element received within the first distal hole is translated proximally along the elongated portion of the first distal hole.

7. The plate of claim 1, wherein the second distal hole is configured as a dynamic compression hole including the sloped compression surface.

8. The plate of claim 1, wherein the proximal portion of the body includes three proximal holes, each of which extends through the proximal portion, from the first surface to the second surface, along a proximal edge thereof, each of the proximal holes being configured to receive a proximal bone fixation element therein.

9. The plate of claim 8, wherein a first one of the three proximal holes extends through the proximal portion in a position configured to facilitate insertion of a first one of the proximal bone fixation elements therethrough into a caudal portion of the proximal segment of the tibia, wherein a second one of the proximal holes extends through the proximal portion in a position configured to facilitate insertion of a second one of the proximal bone fixation elements therethrough into a proximal portion of the proximal segment of the tibia, and wherein a third one of the proximal holes extends through the proximal portion in a position configured to facilitate insertion of a third one of the proximal bone fixation elements therethrough into a cranial portion of the proximal segment of the tibia.

10. A Tibial Plateau Leveling Osteotomy (TPLO) plate for providing a cranial and a distal compression of an osteotomy cut, comprising:
    a body extending longitudinally from a proximal end to a distal end and defined via a first surface which, in an operative configuration, faces away from a bone and a second surface which, in the operative configuration, faces toward the bone, the body including a proximal portion configured to be positioned over a cut and repositioned proximal segment of a tibia during a TPLO procedure and a distal portion extending along a longitudinal axis and configured to be positioned over a distal segment of the tibia during the TPLO procedure;
    a first distal hole extending through the distal portion of the body, proximate the distal end thereof, from the first surface to the second surface, the first distal hole including an elongated portion and an offset portion open to and in communication with one another, the elongated portion extending along the longitudinal axis and the offset portion extending distally from the elongated portion along an offset axis, which extends at an angle relative to the longitudinal axis; and a second distal hole extending through the distal portion of the body proximally of the first distal hole from the first surface to the second surface, the second distal hole extending along the longitudinal axis in alignment with the elongated portion of the first distal hole and including a sloped compression surface along a distal portion thereof, wherein the first distal hole is configured such that when a first distal compression to the osteotomy cut is applied via insertion of a bone fixation element into the distal portion of the second distal hole, a second bone fixation element translates along the offset axis from a central axis to a point of intersection to provide a cranial compression and the first distal compression compression to the osteotomy cut.

11. The plate of claim 10, further comprising:
a third distal hole extending through the distal portion of the body, between the first distal hole and the second distal hole, from the first surface to the second surface and extending along the longitudinal axis, a distal portion of the third distal hole including a sloped compression surface.

12. A method for a Tibial Plateau Leveling Osteotomy (TPLO), comprising:
positioning a bone plate in a desired initial position with a first surface of the bone plate facing away from a tibia and a second surface thereof facing the tibia so that a proximal portion of the bone plate extends over a proximal tibial segment and a distal portion of the bone plate extends over a distal tibial segment that has been cut away from the proximal tibial segment and rotated and seated within a recess formed in the distal tibial segment when the proximal tibia segment was cut away;

inserting a first distal bone fixation element into the distal tibial segment of the tibia along a central axis of an offset portion of a first distal hole, which includes an elongated portion extending along a longitudinal axis of the distal portion of the bone plate and the offset portion extending distally from the elongated portion along an offset axis extending at an angle relative to the longitudinal axis; and inserting a second distal bone fixation element into the distal tibial segment via a second distal hole extending through the distal portion of the bone plate distally of the first distal hole so that a head portion of the second distal bone fixation element slides along a sloped compression surface extending along a distal portion of the second distal hole to move the bone plate distally relative to the second distal bone fixation element and provide a first distal compression between the cut and rotated proximal tibial segment, the first distal bone fixation element translating proximally along the offset axis during the first distal compression so that the bone plate rotates about the second distal bone fixation element and the proximal portion of the bone plate is moved in a cranial direction to provide a cranial compression of the proximal tibial segment against the distal tibial segment.

13. The method of claim 12, wherein the second distal hole extends long the longitudinal axis, in alignment with the elongated portion of the first distal hole.

14. The method of claim 12, wherein, during the cranial compression, the first distal bone fixation element translates along the offset axis from the central axis to a point at which the longitudinal axis and the offset axis intersect.

15. The method of claim 12, further comprising:
inserting a third distal bone fixation element into the distal tibial segment via a third distal hole extending through the distal portion of the bone plate between the first and second distal holes so the head portion of the second distal bone fixation element slides along a sloped compression surface extending along a distal portion of the third distal hole to move the bone plate distally relative to the third distal bone fixation element and provide a second distal compression between the cut and rotated proximal tibial segment and the distal tibial segment.

16. The method of claim 15, wherein the first distal bone fixation element translates proximally along the elongated portion of the first distal hole.

17. The method of claim 15, wherein the third distal bone fixation element extends along the longitudinal axis, in alignment with the second distal hole and the elongated portion of the first distal hole.

18. The method of claim 15, further comprising:
inserting a first proximal bone fixation element through a first proximal hole and a second proximal bone fixation element through a second proximal hole into the proximal tibia segment, the first and second proximal holes extending through the proximal portion of the bone plate so that, when the bone plate is in the desired initial position, the first and second proximal bone fixation elements fix the proximal portion of the bone plate relative to the proximal tibial segment prior to insertion of the second distal bone fixation element through the second distal hole.

19. The method of claim 18, wherein the first proximal bone fixation element is inserted into a cranial side of the proximal tibial segment.

* * * * *